Figure 1:
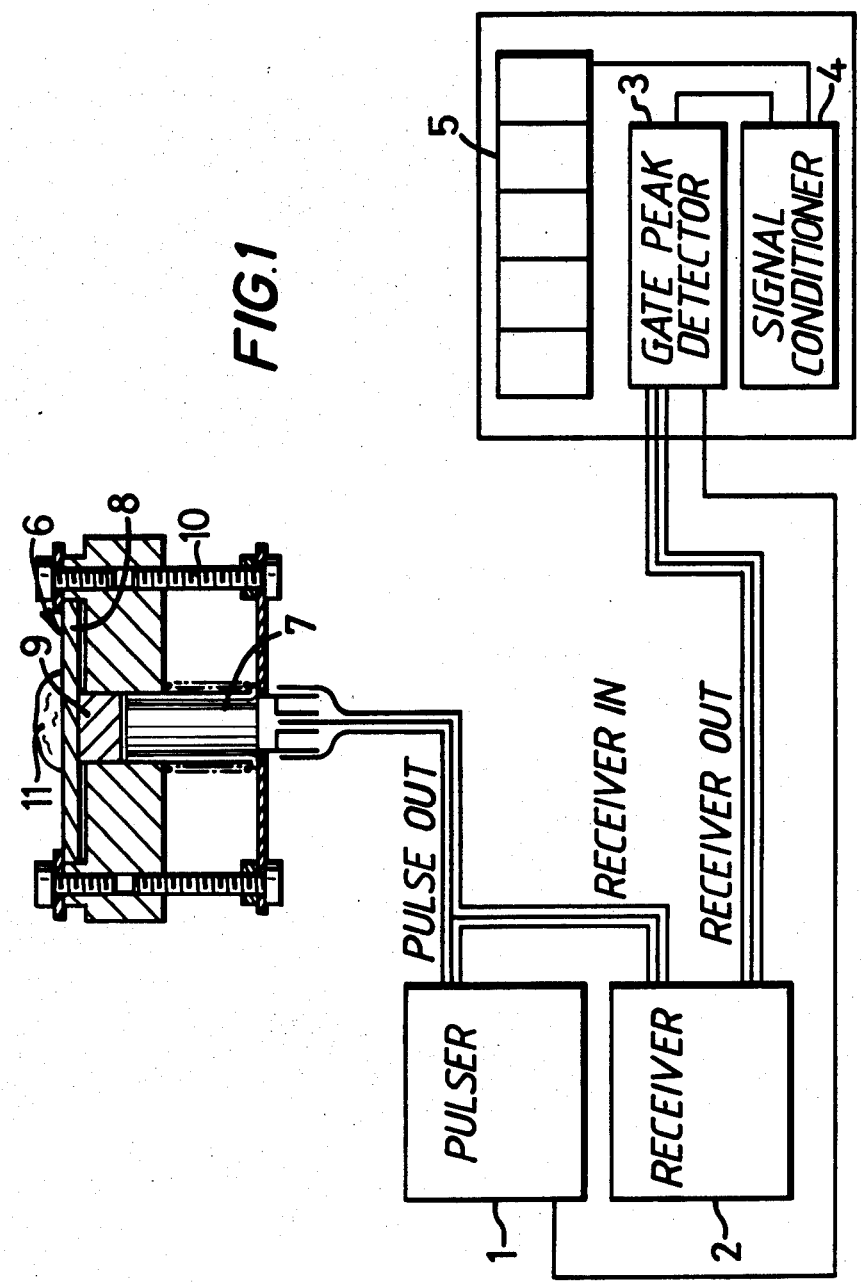

United States Patent [19]

Brown

[11] Patent Number: 4,478,072
[45] Date of Patent: Oct. 23, 1984

[54] APPARATUS FOR DETERMINING THE CONCENTRATION OF SOLIDS DISPERSED IN A LIQUID

[75] Inventor: Harold T. Brown, Ruislip, England

[73] Assignee: The British Petroleum Company p.l.c., London, England

[21] Appl. No.: 430,477

[22] Filed: Sep. 30, 1982

[30] Foreign Application Priority Data

Oct. 9, 1981 [GB] United Kingdom ................. 8130539

[51] Int. Cl.³ ...................... G01N 15/06; G01N 29/00
[52] U.S. Cl. ..................................... 73/61 R; 73/599
[58] Field of Search .............................. 73/599, 61 R

[56] References Cited

U.S. PATENT DOCUMENTS

| | | | |
|---|---|---|---|
| 3,914,984 | 10/1975 | Wade | 73/599 |
| 4,339,944 | 7/1982 | Abts et al. | 73/61 R |
| 4,381,674 | 5/1983 | Abts | 73/599 |
| 4,412,451 | 11/1983 | Uusitalo et al. | 73/599 |

FOREIGN PATENT DOCUMENTS 1550085 8/1979 United Kingdom .

*Primary Examiner*—Howard A. Birmiel
*Attorney, Agent, or Firm*—Morgan Finnegan Pine Foley & Lee

[57] ABSTRACT

An instrument for determining the concentration of solid particles dispersed in a liquid medium, (e.g. coal in oil), comprises (a) an ultrasonic pulser, (b) an ultrasonic receiver, (c) a gated peak detector, (d) signal conditioning and display circuits and (e) an ultrasonic transducer assembly including a layer of known impedance to receive the dispersion. The pulser produces an impulse which is converted by the transducer to an ultrasonic wave, which passes through and is reflected back by the interface between the layer and the dispersion to the ultrasonic receiver and passed to the gated peak detector which measures the peak amplitude of the echo from the layer/dispersion interface. The peak amplitude is then converted by the signal conditioning and display circuits to produce a display of the amplitude and/or the solids content of the dispersion.

5 Claims, 2 Drawing Figures

APPARATUS FOR DETERMINING THE CONCENTRATION OF SOLIDS DISPERSED IN A LIQUID

This invention relates to an apparatus for determining the concentration of solid particles dispersed in a liquid by an ultrasonic technique. The apparatus is particularly suitable for determining the concentration of finely divided coal particles dispersed in a fuel oil medium but is not limited to such an application.

In continuous processes for the production of dispersions of solid particles in liquid media there is the need for a rapid analyser for determining the concentration of the solid particles so that corrective action may be taken if the concentration varies from the desired level.

The British Petroleum Company Limited is developing a process for the production of a stable dispersion of coal in oil. The dispersion is similar to fuel oil in its appearance and handling characteristics and it is difficult to isolate the solid particles from the oil for the purpose of rapid concentration measurements. Gravimetric laboratory methods are available but these, while accurate, are time consuming and not suitable for plant control.

Ultrasonic techniques have been employed for analytical measurement and are useful in providing monitors with electronic readouts. They are rapid in operation and non-destructive of the samples.

Pulse echo techniques for ultrasonic velocity measurement have been devised for determining the concentration of solutes in solvents. However, these are unsatisfactory in relation to solid particles dispersed in liquids because of the higher attenuation of the signal which results. Reverberations can obliterate the desired but weakened echoes.

Another ultrasonic technique depending on velocity measurement using transmission rather than pulse echo has also been proposed to overcome those problems but this suffers from a number of disadvantages including sensitivity to the inorganic content of the coal and to temperature.

An ultrasonic technique has been disclosed for the determination of the coal content of coal oil mixtures by Leffert, Wayne State University. This technique measures the attenuation of ultrasonic waves resulting from passing through the mixture and relates this to the coal concentration.

Attenuation also suffers from a number of disadvantages, however, particularly in the context of industrial usage. Attenuation measurements are affected by the strength of the transmitted signal unless some more complex reference beam is used. The transmitted signal strength may vary as the transducer ages. Also, the presence of gas bubbles can severely affect attenuation because they obscure part of the path. Furthermore, attenuation is dependent upon the particle size.

We have now discovered an ultrasonic technique involving impedance determination which does not suffer from the above disadvantages. The technique is based on the measurement of the reflection coefficient at an interface between a material of known impedance and the material being investigated.

The reflected signal depends on the difference between the impedances of the material of known impedance and the material being investigated. In the case of oil dispersions, for example, the coal has a higher impedance than the oil so the impedance of the mixture increases with coal content. Therefore, as the coal content increases, the difference between the impedance of the coal and the impedance of the mixture decreases. The reflected signal therefore decreases and may be used to indicate coal content.

Thus according to the present invention there is provided an apparatus for the determination of the concentration of solid particles dispersed in a liquid medium which apparatus comprises in combination (a) an ultrasonic pulser, (b) an ultrasonic receiver, (c) a gated peak detector, (d) signal conditioning and display circuits and (e) an ultrasonic transducer assembly including a layer of known impedance to receive the dispersion, the arrangement being such that in use the pulser produces an impulse which is converted by the transducer to an ultrasonic wave which passes through the dispersion and is reflected back by the interface between the layer and the dispersion to the ultrasonic receiver and passed to the gated peak detector which measures the peak amplitude of the echo from the layer/dispersion interface, the peak amplitude then being converted by the signal conditioning and display circuits to produce a display of the peak amplitude and/or the solids content of the dispersion.

The display is preferably digital with the peak amplitude being expressed in volts and/or the solids content being expressed as a percentage by weight.

The layer material is preferably chosen to maximise the sensitivity to small changes in impedance which means that low impedance plastics are more suitable than high impedance materials such as metals. The preferred material is a copolymer of ethylene and hexene sold under the Trade Name Rigidex 002-47.

A suitable transmitting transducer is a piezo-electric ceramic which generates ultrasonic waves at a frequency above 10 KHz, preferably in the range 1 to 10 MHz.

Figure 2:
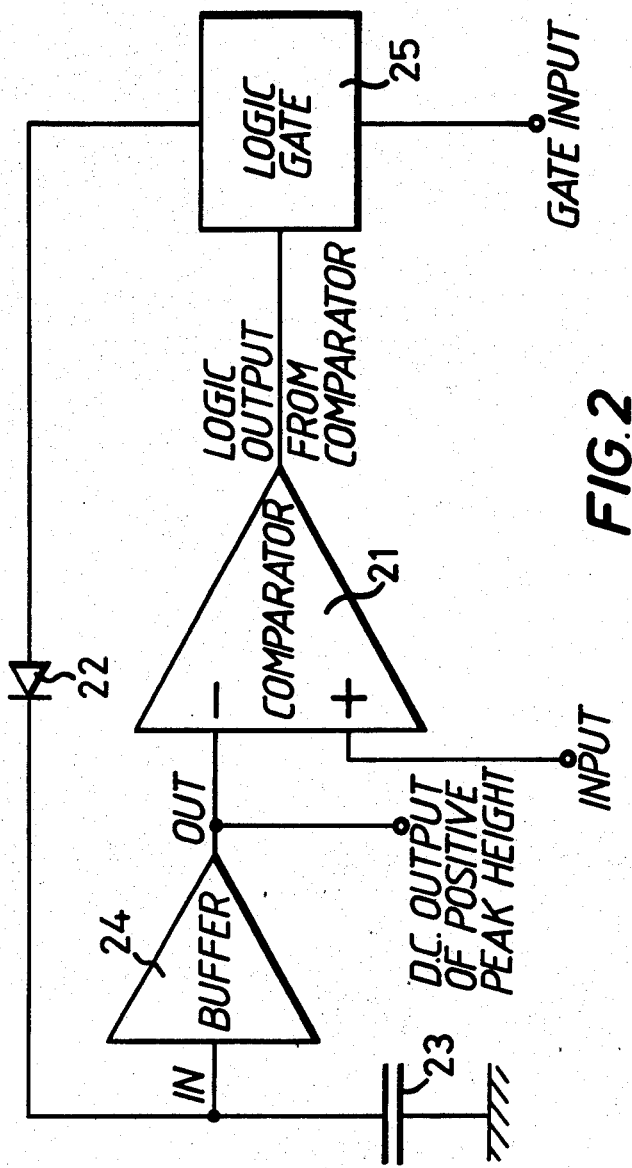

The invention is illustrated with reference to FIGS. 1 and 2 of the accompanying drawings wherein FIG. 1 is a diagram of a batch analyser and FIG. 2 is a schematic diagram of a positive peak detector with time gating in the feedback loop.

The analyser comprises an ultrasonic pulser 1, an ultrasonic receiver 2, a gated peak detector 3, a signal conditioning unit 4, a digital display unit 5 and an ultrasonic transducer assembly 6.

Ultrasonic Pulser 1

The pulser is a "Metrotek Mp215" module. The pulse width is set to low, the damping control is full anti-clockwise and an internal pulse repetition period of 160 μs is used. The pulser produces a negative going impulse whose voltage is adjusted to give an echo of approximately, 1.1 volt from the plastic/air interface.

Ultrasonic Receiver 2

A "Metrotek MR101" receiver is connected to the pulser and the 2.2 MHz transducer in the pulse/echo mode with an attenuator setting of 30dB. The r.f. detector is off and a high pass filter cut-off frequency of 1.0 MHz is used. The output of the receiver is then fed to a purpose built peak detector. All interconnections are made through a Tektronix TM515 main-frame which houses these modules.

Gated Peak Detector 3

The gated peak detector is designed to measure the positive peak amplitude of the second echo which comes from the plastic/coal oil dispersion interface. The time gating is set to gate out all other echoes. The peak detector circuit differs from the conventional gated peak detectors in that the time gating is included in the feedback loop using logic elements rather than using time gating of the signals at the input to the peak detector. This arrangement avoids the usual problems of capacitive coupling between the gate and the analogue input signals which cause transients and steps in the gated signal.

Signal Conditioning 4 and Display 5

The signal conditioning and display circuits are designed to produce a digital display of either the peak amplitude in volts or coal content in % weight. The "cal" control adjusts the gain of the volts output to allow setting to 1 volt in air. The coal content is derived for a limited range by assuming a linear relationship between reflected signal and coal content. The slope and offset of this calibration may be adjusted by the "slope" and "preset content" controls respectively.

Ultrasonic Transducer Assembly 6

The ultrasonic transducer 7 ("Panametrics V306 SB" 2.2 MHz ½" diameter) is acoustically coupled to a 3 mm thick disc of the "Rigidex" copolymer (002-47) 8 using a plug of silicone high vacuum grease 9 and housed in a brass assembly 10. A sample 11 of the material the concentration of which is to be determined is placed on the disc 8.

When compared with other techniques such as density or ultrasonic velocity measurement the technique is:

(i) Less sensitive to temperature because the measurement is essentially a comparison between the properties of the plastic and the dispersion. Variation in the velocity and density of the dispersion is compensated for by a similar variation with temperature in the plastic.

(ii) Less sensitive to variations in coal velocity of sound and density.

(iii) Ideally suited to small sizes and quick to use.

The pulse technique is used because with time gating, the effects of reverberation (multiple echoes) can be avoided. In continuous wave techniques, reverberations would cause errors in the signal.

The use of plastic is important for two reasons:
(i) The material is similar acoustically to the coal oil dispersions. This improves the sensitivity.
(ii) The temperature dependance of its acoustic properties are similar to those of the dispersion which, as described above, make the measurement relatively insensitive to temperature.

The use of a separate reflector, rather than the transducer face itself, permits the independent selection of the reflector material.

The gated peak detector uses time gating in the feed back loop to avoid the problems of transients and steps normally associated with time gating in the input signal path.

With reference to FIG. 2, the input signal is fed to the positive input of comparator 21 whose output is low when the positive input is lower in voltage than the negative input connection. If the positive input rises above the negative input the comparator output goes high and forward biases the feedback diode 22 to charge the storage capacitor 23 until the buffered voltage, which is fed to the negative input, is equal to the voltage on the positive input. Then the comparator output will go low and the diode no longer conducts. Thus the storage capacitor is charged such that the signal at the negative comparator input is equal to the highest positive voltage at the positive input. This signal on the negative input may therefore be used as the peak detector output. The buffer 24 reduces leakage of charge from the storage capacitor to allow the peak signal to be held for the period of time between pulses. A logic gate 25 in the feedback loop is used to gate out the unwanted pulses by producing a low output when the gate input is taken low.

I claim:

1. Apparatus for the determination of the concentration of solid particles dispersed in a liquid medium which apparatus comprises in combination (a) an ultrasonic pulser, (b) an ultrasonic receiver, (c) a gated peak detector, (d) signal conditioning and display circuits and (e) an ultrasonic transducer assembly including a layer of known impedance far contacting the dispersion, the arrangement being such that in use the pulser produces an impulse which is converted by the transducer to an ultrasonic wave which is directed towards the layer and the dispersion and a second ultrasonic wave is reflected back by the interface between the layer and the dispersion to the ultrasonic receiver and passed to the gated peak detector which measures the peak amplitude of the echo from the layer dispersion interface, the peak amplitude then being converted by the signal conditioning and display circuits to produce a display of the peak amplitude, the solids content, or the peak amplitude and the solids content of the dispersion.

2. Apparatus according to claim 1 wherein the layer of known impedance is fabricated from a copolymer of ethylene and hexene.

3. Apparatus according to claim 1 wherein the ultrasonic pulser comprises a piezoelectric ceramic.

4. Apparatus according to claim 1 wherein the layer of known impedance includes a substantially flat plate.

5. Apparatus according to claim 1 which further includes a layer of grease between the layer of known impedance and the ultrasonic pulser.

* * * * *